(12) United States Patent
Li et al.

(10) Patent No.: US 10,667,707 B2
(45) Date of Patent: Jun. 2, 2020

(54) MICROANGIOGRAPHY METHOD AND SYSTEM BASED ON FULL-SPACE MODULATION SPECTRUM SPLITTING AND ANGLE COMPOUNDING

(71) Applicant: ZHEJIANG UNIVERSITY, Hangzhou, Zhejiang (CN)

(72) Inventors: Peng Li, Zhejiang (CN); Pei Li, Zhejiang (CN); Yuxuan Cheng, Zhejiang (CN); Liping Zhou, Zhejiang (CN); Zhihua Ding, Zhejiang (CN)

(73) Assignee: ZHEJIANG UNIVERSITY, Hangzhou, Zhejiang (CN)

( * ) Notice: Subject to any disclaimer, the term of this patent is extended or adjusted under 35 U.S.C. 154(b) by 387 days.

(21) Appl. No.: 15/547,922

(22) PCT Filed: Apr. 20, 2016

(86) PCT No.: PCT/CN2016/079693
§ 371 (c)(1),
(2) Date: Aug. 1, 2017

(87) PCT Pub. No.: WO2017/133083
PCT Pub. Date: Aug. 10, 2017

(65) Prior Publication Data
US 2018/0070842 A1    Mar. 15, 2018

(30) Foreign Application Priority Data
Feb. 5, 2016    (CN) .......................... 2016 1 0080511

(51) Int. Cl.
*G01B 9/02* (2006.01)
*A61B 5/0275* (2006.01)
(Continued)

(52) U.S. Cl.
CPC ........ *A61B 5/02755* (2013.01); *A61B 5/0066* (2013.01); *A61B 5/0079* (2013.01);
(Continued)

(58) Field of Classification Search
CPC ..... A61B 5/026; A61B 5/0261; A61B 5/0066; A61B 5/7235; A61B 5/7275; A61B 3/102;
(Continued)

(56) References Cited

U.S. PATENT DOCUMENTS

2013/0242309 A1* 9/2013 Yuan .................. G01B 9/02004
356/479
2014/0228681 A1* 8/2014 Jia ...................... G01B 9/02091
600/425

OTHER PUBLICATIONS

Evaluation of complex conjugate artifact removal methods used in spectrometer-based Fourier-domain optical coherence tomography systems: a comparative study, Optical Coherence Tomography and Coherence Domain Optical Methods in Biomedicine XIV, Proc. of SPIE vol. 7554, 75542X (Year: 2010).*

* cited by examiner

*Primary Examiner* — Tarifur R Chowdhury
*Assistant Examiner* — Jonathon Cook

(57) ABSTRACT

A microangiography method and system based on full-space modulation spectrum splitting and angle compounding is disclosed. Label-free three-dimensional optical coherence tomography angiography is realized by combining the three-dimensional space resolution capability of an optical coherence tomography and the motion recognition capability of a dynamic scattering technology. Probe light of different incident angles is encoded with a transverse scanning modulation spectrum in a spatial frequency domain, incident angle-resolved sub-angiograms which are independent of one another are obtained by splitting the modulation spectrum, (Continued)

and an angiogram with multiple space angles compounded is realized. Conjugate mirror images are removed from a depth (z) domain, a complex-valued OCT interference spectra are reconstructed, the full-space modulation spectrum is obtained in the spatial frequency domain, and the overlap of the modulation spectrum conjugate mirror images is avoided. And the absolute flow velocity of blood flow can be measured through a multi angle-resolved probing technology.

3 Claims, 3 Drawing Sheets

(51) Int. Cl.
    *A61B 5/00*          (2006.01)
    *A61B 5/026*        (2006.01)
    *A61B 3/10*          (2006.01)

(52) U.S. Cl.
    CPC .......... *A61B 5/0261* (2013.01); *A61B 5/7235* (2013.01); *A61B 5/7275* (2013.01); *G01B 9/02044* (2013.01); *G01B 9/02083* (2013.01); *G01B 9/02091* (2013.01); *A61B 3/102* (2013.01); *G06T 2207/10101* (2013.01)

(58) Field of Classification Search
    CPC ............ G01B 9/02044; G01B 9/02083; G01B 9/02091; G06T 2207/10101; G06T 2207/20048; G06T 2207/20216; G06T 2207/30101; G06T 2207/30104
    See application file for complete search history.

MICROANGIOGRAPHY METHOD AND SYSTEM BASED ON FULL-SPACE MODULATION SPECTRUM SPLITTING AND ANGLE COMPOUNDING

CROSS REFERENCE OF RELATED APPLICATION

This is a U.S. National Stage under 35 U.S.C 371 of the International Application PCT/CN2016/079693, filed Apr. 20, 2016, which claims priority under 35 U.S.C. 119(a-d) to CN 201610080511.8, filed Feb. 5, 2016.

BACKGROUND OF THE PRESENT INVENTION

Field of Invention

The present invention relates to OCT (Optical Coherence Tomography) and label-free three-dimensional optical coherence tomography angiography (OCT Angiography; OCTA) based on OCT, and more particularly to a microangiography method and system based on full-space modulation spectrum splitting and angle compounding.

Description of Related Arts

OCT is a new imaging technique that has gradually developed since 1990s, which has significant applications in Biomedicine field. OCT draws attention from research workers from China and abroad to carry out further research by the advantages of label-free, non-invasive and non-contact characteristics, high resolution and high detective sensitivity, which has wide application in clinical treatment. OCT detects a change in intensity of backscattered light from the test sample caused by the optical unevenness of the biological sample to obtain the reflectivity within the test sample and reconstruct a cross-sectional image of the sample. Usually, at an early stage of the disease, the light scattering difference between normal and diseased biological tissue is minor, which is difficult to be detected and distinguished by the conventional structural OCT. So the conventional structural OCT has limited applications in clinical treatment. In order to obtain more physiological information other than biological sample tissue morphology, functional OCT is widely applied and developed.

Many diseases (including ocular fundus diseases such as glaucoma and age-related macular degeneration and brain diseases such as stroke) are closely related to pathological changes of perfusion. Monitoring patient's blood vessels in real time, which provides three-dimensional image of the blood vessels, is important for early diagnosis and treatment of the diseases. OCTA is a promising technique which is able to assist diagnosis of blood vessel disease and distinguish static tissue and dynamic blood flow signal. OCTA extends the function of OCT in obtaining blood flow information inside the blood vessel. Compared to conventional imaging technique, OCTA doesn't require a contrast agent and X-ray while has three-dimensional depth-resolved high-contrast imaging capability for microvascular by extending the OCT technique. Conventionally, a blood flow contrast model is established by analyzing the temporal statistical characteristics of the light scattering signal by mathematical procedure and thresholding splitting of the dynamic blood flow signal and static tissue background signal. The overlap between the dynamic and static signal statistic curve causes mistakes when distinguishing dynamic and static signals and suppress the blood flow contrast. The imaging feature is better illustrated and explained by enhancing the blood flow contrast in OCTA with effective methods.

Based on researches about the temporal statistical characteristics of OCTA signal, the following conclusions are made: the average of multiple independent sub-angiorams is able to improve the imaging contrast. Independent sub-angiograms are able to be obtained through wavelength diversity, angle diversity, polarization diversity and etc. referring to speckle eliminating methods. Jia and his team members proposed a spectrum-split OCTA method similar to wavelength diversity. The method segments the full wavelength spectrum of OCT interference signals into different subspectra. Each subspectrum is able to generate independent sub-angiograms which are combined to a new angiogram. Compared to the original full wavelength spectrum, the bandwidth of each subspectrum is narrowed, which leads to degradation of axial resolution.

SUMMARY OF THE PRESENT INVENTION

An object of the present invention is to provide a microangiography method and system based on full-space modulation spectrum splitting and angle compounding to overcome the disadvantages of the conventional technique.

A microangiography method based on full-space modulation spectrum splitting and angle compounding, comprising following steps:

1) reconstructing complex-valued interference spectrum and obtaining a full-space transverse scanning modulation spectrum in a spatial frequency domain by removing conjugate mirror images in a OCT (Optical Coherence Tomography) depth (z) domain;

2) encoding a probe light of different incident angles with the transverse scanning modulation spectrum in the spatial frequency domain and obtaining incident angle-resolved OCT interference subspectra which is independent of one another by splitting the modulation spectrum;

3) obtaining independent angle-resolved sub-angiograms based on the transverse scanning modulation spectrum splitting by combing a modulation spectrum splitting technology and an optical microangiography technology in step 2);

4) obtaining multi-angle resolved independent sub-angiograms based on a full-space transverse scanning modulation spectrum splitting by combining the full-space modulation spectrum in step 1) and the modulation spectrum splitting technology and the optical microangiography technology in step 2), and 5) averaging the sub-angiograms obtained in step 3) or step 4) to get an angiogram with multiple space angles compounded.

A multi-angle resolved absolute flow velocity of blood flow is measured based on the transverse scanning modulation spectrum splitting through the modulation spectrum splitting technology in step 2).

A multi-angle resolved absolute flow velocity of blood flow is measured based on the full-space transverse scanning modulation spectrum splitting through the full-space modulation spectrum in step 1) and the modulation spectrum splitting technology in step 2).

The object of the present invention is realized by the following technical solution:

A microangiography method based on full-space modulation spectrum splitting and angle compounding:

1) In OCT imaging, the real-valued interference spectrum signal obtained by a transverse scan is denoted as S (k,x), where k is the wave number, x is the transverse fast-scan direction. Direct Fourier-transform of the real-valued spectrum signal along the x direction leads to aliasing of the positive and negative frequency of the obtained spatial frequency, which requires a reconstruction of complex-valued OCT interference spectrum. The spatial structure information of depth domain (z) is calculated by a Fourier-transform from real-valued spectrum S (k,x) along k direction to reconstruct the complex-valued spectrum. Usually in spectral domain OCT, half of the z space corresponds to a ~3 mm imaging range which is able to satisfy most application requirements. So by placing the test sample on one side of zero optical length difference, the complex conjugate mirror images are able to be distinguished. By removing one conjugate term in the z domain and inverse Fourier-transform along k direction, the complex-valued spectrum signal S % (k,x) is finally obtained. A full-space transverse scanning modulation spectrum in the spatial frequency domain is obtained by a Fourier-transform from the complex spectrum along the x direction.

2) In the sample arm of the OCT system, usually the diameter of the light beam that hits on the objective is required to be as large as possible to obtain a high transverse imaging resolution. So when a collimating light beam of a certain width irradiates the center of the rotational axis of the sample arm scanning mirror, the offset δ occurs from the light beam to the center of the rotational axis. The offset δ induces the sample arm optical path modulation, which leads to the transverse scanning modulation in the spatial frequency domain. The modulation frequency $f_m$ and offset δ is in a linear function:

$$f_m = \frac{2k\delta\omega}{\pi},$$

Where k is the central wave number of the light source, and co is the angular velocity of the scanning mirror. In the full-space transverse scanning modulation spectrum, different modulation frequency corresponds to the probe light of different incident angle. The angle-resolved independent OCT interference subspectra are obtained by splitting of the modulation spectrum. The number and overlap of the subspectra obtained by splitting are decided by the image effect: more subspectra lead to lower transverse resolution and increased processing algorithm complexity; a large overlap area between the subspectra leads to correlation between the adjacent subspectra, which effects the encoding of the probe light of different incident angles.

3) Independent sub-angiograms are able to be generated respectively from the incident angle-resolved independent subspectra by adopting the conventional microangiography methods such as amplitude difference method, complex difference method, decorrelation method, speckle variance method and etc. A new angiogram is able to be obtained by averaging and compounding the spatial angle-resolved sub-angiograms.

The conventional method of measuring flow velocity from Doppler shift is limited to measure the velocity component which is parallel with the probe light. In order to measure the absolute flow velocity of the blood flow, Doppler angle (the angle between probe light and blood flow) is required. Probe light of different incident angle is able to be distinguished based on the full-space modulation spectrum splitting. Flow velocity component of different incident angle which parallels with the probe direction is able to be obtained by adopting Doppler blood flow velocity calculation method to work on the angle-resolved modulation subspectra from splitting. The absolute blood flow velocity is able to be further determined according to the geometric relationship.

A microangiography system based on full-space modulation spectrum splitting and angle compounding, comprising a low-coherence broad-bandwidth light source, an optical circulator, a coupler, a reference arm, a sample arm, a spectroscope and a signal processing module; wherein the reference arm comprises a reference arm polarization control device, a reference arm collimating lens, a reference arm focusing lens and a flat mirror; the sample arm comprises a sample arm polarization control device, a sample arm collimating lens, an orthogonal scanning mirror and a sample arm focusing objective; the spectroscope comprises a spectroscope collimating lens, a blazed grating, a Fourier lens and a CMOS (Complementary Metal-Oxide-Semiconductor) linear array camera;

The low-coherence broad-bandwidth light source is connected to an input end at a first side of the coupler through the optical circulator; a first output port of a second side of the coupler is connected to the reference arm collimating lens through the reference arm polarization control device; an optical axis of the reference arm focusing lens is coincident with an axis of the reference arm collimating lens; the flat mirror is placed on a focal plane of the reference arm focusing lens; a second output port of the second side of the coupler is connected to the sample arm collimating lens through the sample arm polarization control device; the orthogonal scanning mirror comprise a first mirror and a second mirror, wherein a center of a first mirror's rotational axis is on an optical axis of the sample arm collimating lens and a center of a second mirror's axis is on an optical axis of the sample arm focusing objective; a test sample is placed on a focal plane of the sample arm focusing objective; an output port of the optical circulator is connected to the spectroscope collimating lens; the blazed grating is placed on an optical path of emergent light of the spectroscope collimating lens based on spectrophotometry; the Fourier lens is placed on an optical path of emergent light of the blazed grating; a light intake plane of the CMOS linear array camera is coincident with a back focal plane of the Fourier lens; the signal processing module is connected to a back of the CMOS linear array camera;

A beam of light radiating from the low-coherence broad-bandwidth light source is incident onto the coupler through the optical circulator; an outgoing light beam is split into two parts, wherein one part enters the reference arm and hits the flat mirror after being collimated and focused; another part enters the sample arm and hits the test sample after being collimated and focused; the orthogonal scanning mirror of the reference arm performs a three-dimensional scanning on the test sample by a beam of sample arm light; interference occurs between reflected light from the flat mirror of the reference arm and backscattered light from the test sample at the coupler; outgoing light interferences through the spectroscope are collected and processed by the signal processing module.

Compared with the conventional technology, the advantages of the present invention are as follow:

1) The multiple space angle-compounded angiogram obtained by adopting the present invention has enhanced contrast and blood vessel connectivity.

2) The conventional spectrum-splitting OCTA method which is similar to the wavelength diversity leads to degradation of axial resolution while splitting the spectrum. The present invention has no effects on the axial resolution.

3) The full-space transverse modulation spectrum splitting technique in the present invention is able to provide maximum transverse modulation spectrum of the spatial frequency domain and prevent the transverse resolution degradation due to the modulation spectrum splitting.

4) The multi-angle resolved probe technique based on the full-space modulation spectrum splitting in the present invention is able to realize the measurement of absolute flow velocity of blood flow with single beam and single measurement.

Figure 1:
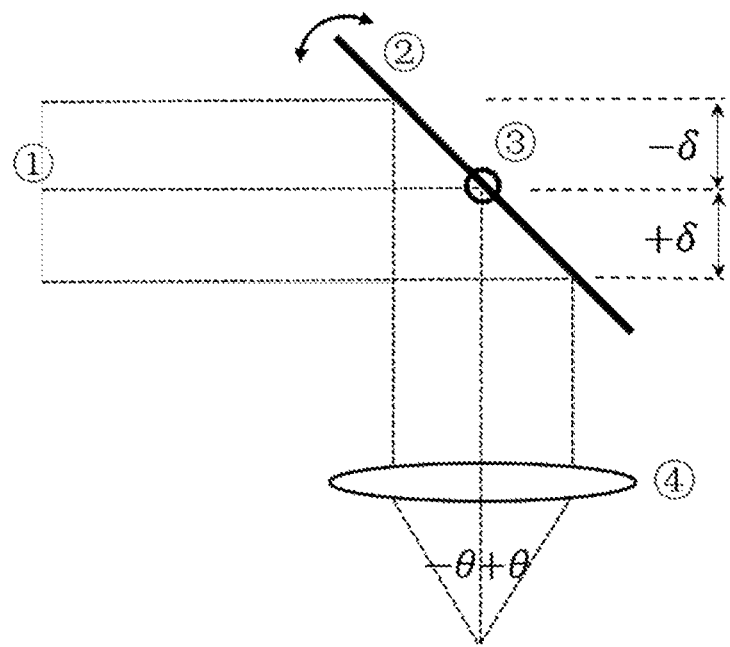
FIG. 1 is a perspective view of a sample arm scanning beam.
Figure 2:
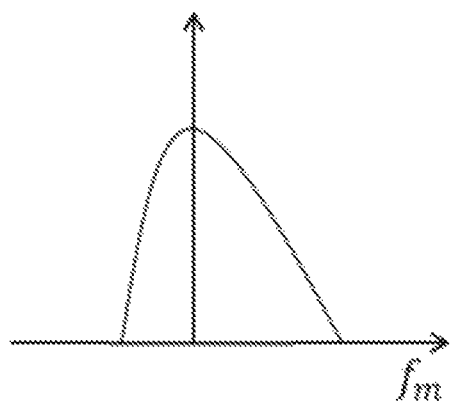
FIG. 2 is a graph of modulation frequency $f_m$ for offset $\delta$.
Figure 3:
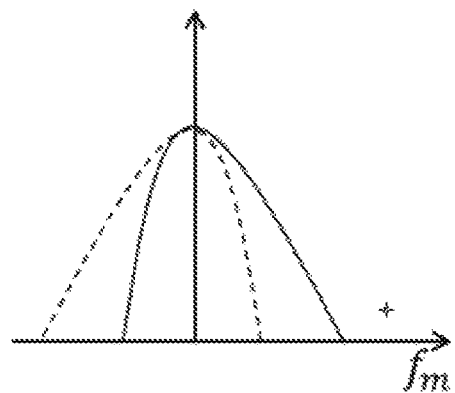
FIG. 3 is the aliasing graph of positive and negative frequency of a transverse scanning modulation spectrum.
Figure 4:
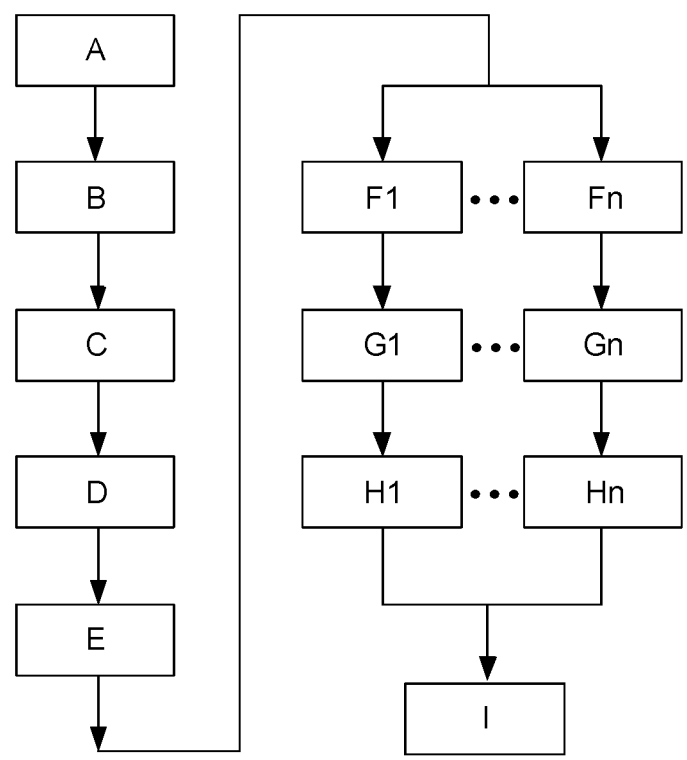
FIG. 4 is a flow chart to illustrate a method of the present invention.
Figure 5:
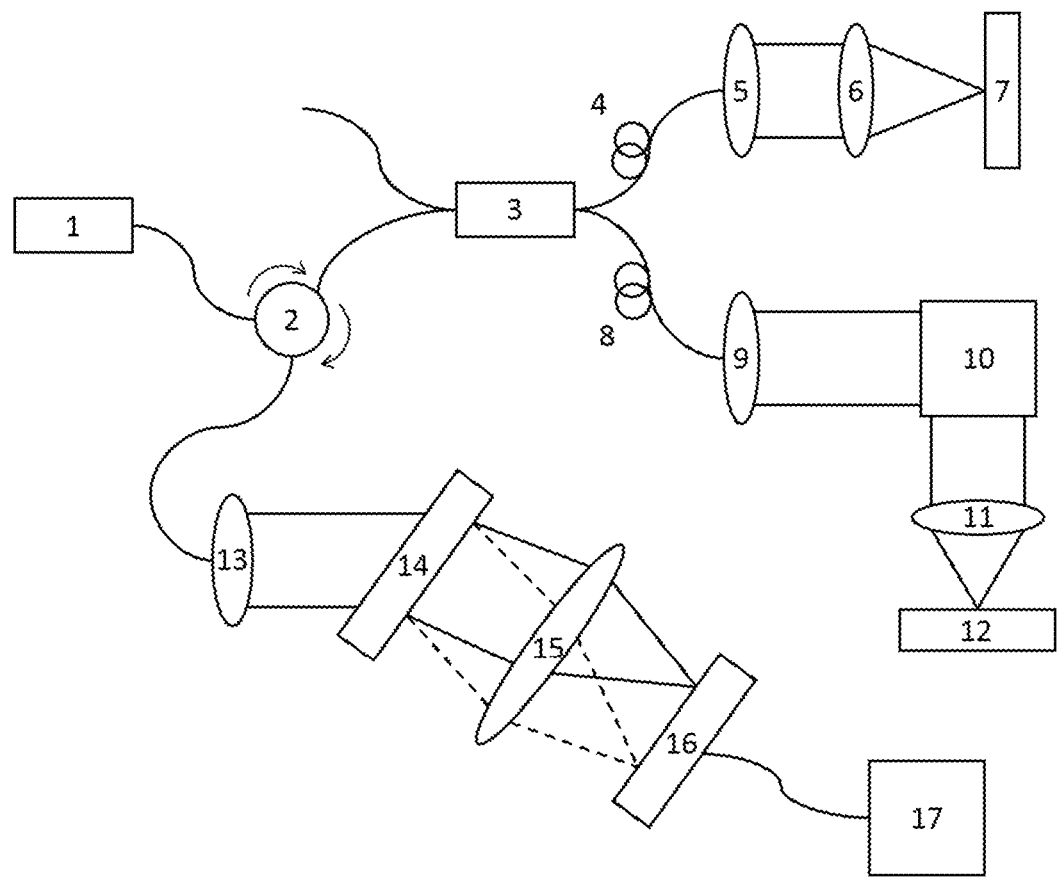
FIG. 5 is a perspective view of the imaging system of the present invention.

Elements in FIG. 1: ① probe light beam; ② scanning mirror; ③ center of the rotational axial of the scanning mirror; ④ focusing objective;

In FIG. 2: the modulation frequency $f_m$ for introducing the offset $\delta$;

In FIG. 3 the aliasing of the positive and negative frequency of the transverse scanning modulation spectrum;

In FIG. 4: A denotes a real-valued OCT interference spectrum signal; B denotes a spatial structure along depth (z); C denotes a spatial structure after removing the conjugate term; D denotes a complex-valued interference spectrum; E denotes a full-space transverse scanning modulation spectrum of a spatial frequency domain; F1 to Fn denotes modulation subspectra obtained from splitting respectively; G1 to Gn denotes spatial structure signals in z domain respectively; H1 to Hn denotes OCT sub-angiograms respectively; I denotes OCT angiogram;

In FIG. 5: 1. low-coherence broad-bandwidth light source; 2. optical circulator; 3. coupler; 4. reference arm polarization control device; 5. reference arm collimating lens; 6. reference arm focusing lens; 7. flat mirror; 8. sample arm polarization control device; 9. sample arm collimating lens; 10. orthogonal scanning mirror; 11. sample arm focusing objective; 12. test sample; 13. collimating lens; 14. blazed grating; 15. Fourier lens; 16. CMOS linear array camera; 17. signal processing module.

DETAILED DESCRIPTION OF THE PREFERRED EMBODIMENT

Referring to the drawings, according to a preferred embodiment of the present invention is illustrated, wherein FIG. 1, FIG. 2 and FIG. 3 are illustrations of a transverse modulation theory of the present invention. Detailed explanations on FIG. 1, FIG. 2 and FIG. 3 are as below:

1) In the sample arm of the OCT system, usually the diameter of the light beam that hits on the objective is required to be as large as possible to obtain a high transverse imaging resolution. So, in FIG. 1, when a wide light beam is collimated on the center of the rotational axis of the sample arm scanning mirror, an offset $\delta$ occurs from the light beam to the center of the rotational axis. The offset $\delta$ induces the sample arm optical path modulation, which leads to the transverse scanning modulation in the spatial frequency domain (as shown in FIG. 2). The modulation frequency $f_m$ and offset $\delta$ is in a linear function:

$$f_m = \frac{2k\delta\omega}{\pi},$$

Where k is the central wave number of the light source, and co is the angular velocity of the scanning mirror. In the full-space transverse scanning modulation spectrum, different modulation frequency corresponds to the probe light of different incident angle.

2) In OCT imaging, a real-valued signal corresponds to the interference spectrum obtained by a transverse scan. Direct Fourier-transform of the real-valued spectrum signal along the fast-scan direction leads to aliasing of the positive and negative frequency of the obtained spatial frequency (as in FIG. 3), which requires a reconstruction of the complex-valued OCT interference spectrum.

FIG. 4 is a flow chart to illustrate the implementation of the method of the present invention. Detailed explanation on the processes in the FIG. 4 is as below:

1) In OCT imaging, a real-valued signal corresponds to the interference spectrum obtained by a transverse scan (as in box A). The spatial structure information in the depth domain (z) (as in box B) is calculated by a Fourier-transform from real-valued spectrum along the wave number k direction to reconstruct the complex-valued spectrum signal. Usually in the spectral domain OCT, a half of the z space corresponds to a 3 mm imaging range which is able to satisfy most application requirements. So, by placing the test sample on one side of zero optical length difference, the complex conjugate mirror images are able to be distinguished. By removing the conjugate term in the z domain and inverse Fourier-transform along k direction, the complex-valued spectrum signal S % (k,x) (as in box D) is finally obtained. A full-space transverse scanning modulation spectrum (as in box E) in the spatial frequency domain is obtained by a Fourier-transform from the complex-valued spectrum along the x direction.

2) The incident angle-resolved independent OCT interference subspectra (as in box F1 to Fn) are obtained by splitting of the modulation spectrum. The number n and overlap of the subspectra obtained by splitting are decided by the image effect: more subspectra lead to lower transverse resolution and increased processing algorithm complexity; a large overlap area between the subspectra leads to correlation between the subspectra, which effects the encoding of the probe light of different incident angles.

3) The z domain spatial structure information (as in box G1 to Gn) is obtained by inverse Fourier-transform of the incident angle-resolved independent subspectra (as in box F1 to Fn) along the x direction respectively and then Fourier-transform along the k direction. Independent sub-angiograms (as in box H1 and Hn) are generated respectively from the incident angle-resolved independent subspectra by adopting the conventional microangiography methods such as amplitude difference method, cross-correlation method and etc. A new angiogram (as in box I) is obtained by averaging and compounding the spatial angle-resolved sub-angiograms, in which the blood flow contrast is improved.

The conventional method of measuring flow velocity from Doppler shift is limited to measure the velocity component which is parallel with the probe light. In order to measure the absolute flow velocity of the blood flow, Doppler angle (the angle between probe light and blood flow) is required. Probe light of different incident angle is able to be distinguished based on the full-space modulation spectrum splitting. Flow velocity component of different incident angle which parallels with the probe direction is able to be obtained by adopting Doppler blood flow velocity calculation method to work on the modulation subspectra from splitting (as in box F1 and Fn). The absolute blood flow velocity is able to be further determined according to the geometric relationship.

FIG. 5 is an illustration of the imaging system of the present invention. Detailed explanations of FIG. 5 are as below:

The microangiography system based on full-space modulation spectrum splitting and angle compounding, comprising a low-coherence broad-bandwidth light source 1, an optical circulator 2, a coupler 3, a reference arm, a sample arm, a spectroscope and a signal processing module 17; wherein the reference arm comprises a reference arm polarization control device 4, a reference arm collimating lens 5, a reference arm focusing lens 6 and a flat mirror 7; the sample arm comprises a sample arm polarization control device 8, a sample arm collimating lens 9, an orthogonal scanning mirror 10 and a sample arm focusing objective 11; the spectroscope comprises a spectroscope collimating lens 13, a blazed grating 14, a Fourier lens 15 and a CMOS (Complementary Metal-Oxide-Semiconductor) linear array camera;

wherein the low-coherence broad-bandwidth light source 1 is connected to an input end at a first side of the coupler 3 through the optical circulator 2; a first output port of a second side of the coupler 3 is connected to the reference arm collimating lens 5 through the reference arm polarization control device 4; an optical axis of the reference arm focusing lens 6 is coincident with an axis of the reference arm collimating lens 5; the flat mirror 7 is placed on a focal plane of the reference arm focusing lens 6; a second output port of the second side of the coupler 3 is connected to the sample arm collimating lens 9 through the sample arm polarization control device 8; the orthogonal scanning mirror 10 comprise a first mirror and a second mirror, wherein a center of a first mirror's rotational axis is on an optical axis of the sample arm collimating lens 9 and a center of a second mirror's axis is on an optical axis of the sample arm focusing objective 11; a test sample 12 is placed on a focal plane of the sample arm focusing objective 11; an output port of the optical circulator 2 is connected to the spectroscope collimating lens 13; the blazed grating 14 is placed on an optical path of emergent light of the spectroscope collimating lens 13 based on spectrophotometry; the Fourier lens 15 is placed on an optical path of emergent light of the blazed grating 14; a light intake plane of the CMOS linear array camera 16 is coincident with a back focal plane of the Fourier lens 15; the signal processing module 17 is connected to a back of the CMOS linear array camera 16;

a beam of light radiating from the low-coherence broad-bandwidth light source 1 is incident onto the coupler 3 through the optical circulator 2; an outgoing light beam is broken into two parts, wherein one part enters the reference arm and hits the flat mirror 7 after being collimated and focused; another part enters the sample arm and hits the test sample 12 after being collimated and focused; the orthogonal scanning mirror 10 of the reference arm performs a three-dimensional scanning on the test sample 12 by a beam of sample arm light; interference occurs between reflected light from the flat mirror 7 of the reference arm and backscattered light from the test sample 12 at the coupler 3; outgoing light interferences through the spectroscope are collected and processed by the signal processing module 17.

What is claimed is:

1. A microangiography method based on full-space modulation spectrum splitting and angle compounding, comprising following steps of:
   1) reconstructing complex-valued interference spectrum and obtaining a full-space transverse scanning modulation spectrum in a spatial frequency domain by removing conjugate mirror images in an OCT (Optical Coherence Tomography) depth (z) domain;
   2) encoding a probe light of different incident angles with the full-space transverse scanning modulation spectrum in the spatial frequency domain and obtaining an incident angle-resolved OCT interference subspectra independent of one another by splitting a modulation spectrum;
   3) obtaining independent sub-angiograms of multi-angle-resolved based on transverse scanning modulation spectrum splitting by combing a modulation spectrum splitting technology and an optical coherence tomography angiography technology in the step 2);
   4) obtaining multi angle-resolved independent sub-angiograms based on full-space transverse scanning modulation spectrum splitting by combining a full-space modulation spectrum in the step 1) and the modulation spectrum splitting technology and the optical coherence tomography angiography technology in the step 2), and
   5) averaging the sub-angiograms obtained in the step 3) or the step 4) to get a angiogram with multiple space angles compounded.

2. The microangiography method based on the full-space modulation spectrum splitting and angle compounding, as recited in claim 1, wherein a multi angle-resolved absolute flow velocity of blood flow is measured based on the transverse scanning modulation spectrum splitting through the modulation spectrum splitting technology in the step 2).

3. The microangiography method based on full-space modulation spectrum splitting and angle compounding, as recited in claim 1, wherein a multi-angle-resolved absolute flow velocity of blood flow is measured based on the full-space transverse scanning modulation spectrum splitting through the full-space modulation spectrum in the step 1) and the modulation spectrum splitting technology in the step 2).

* * * * *